US011045536B2

United States Patent
Graves et al.

(10) Patent No.: US 11,045,536 B2
(45) Date of Patent: Jun. 29, 2021

(54) VACCINE

(71) Applicant: OZQ PTY LTD, Highton (AU)

(72) Inventors: Stephen Roger Graves, New Lambton (AU); John Stenos, Highton (AU); Moira Cecelia Graves, New Lambton (AU); Rudolf Toman, Bratislava (SK); Rodney Carbis, Strathmore (AU)

(73) Assignee: OZQ PTY LTD, Highton (AU)

( * ) Notice: Subject to any disclaimer, the term of this patent is extended or adjusted under 35 U.S.C. 154(b) by 0 days.

(21) Appl. No.: 16/762,067

(22) PCT Filed: Nov. 6, 2018

(86) PCT No.: PCT/AU2018/051200
§ 371 (c)(1),
(2) Date: May 6, 2020

(87) PCT Pub. No.: WO2019/084632
PCT Pub. Date: May 9, 2019

(65) Prior Publication Data
US 2020/0345824 A1 Nov. 5, 2020

(30) Foreign Application Priority Data
Nov. 6, 2017 (AU) ................................ 2017904499

(51) Int. Cl.
*A61K 39/02* (2006.01)
*A61K 47/64* (2017.01)
*A61P 31/04* (2006.01)
*A61K 39/385* (2006.01)
*A61K 39/00* (2006.01)

(52) U.S. Cl.
CPC ........ *A61K 39/0208* (2013.01); *A61K 39/385* (2013.01); *A61K 47/646* (2017.08); *A61P 31/04* (2018.01); *A61K 2039/6037* (2013.01); *A61K 2039/62* (2013.01)

(58) Field of Classification Search
None
See application file for complete search history.

(56) References Cited

PUBLICATIONS

International Search Report and Writen Opinion in PCT/AU2018/051200, dated Dec. 20, 2018.
Toman, R et al. "Recent progress in glycomics and proteomics of the Q fever bacterium *Coxiella burnetii*"; Acta Virological (2013), vol. 57: 229-237.
Vadovic, P et al. "Structural and Functional Characterization of the Glycan Antigens Involved in Immunobiology of Q Fever"; Ann. N.Y. Acad. Sci. (2005), vol. 1063: 149-153.
Slabá, K et al. "Studies on the Immunological Role of Virenose and Dihydrohydroxystreptose Present in the *Coxiella burnetii* Phase I Lipopolysaccharide"; Ann. N.Y. Acad. Sci. (2003); vol. 990: 505-509.
Hotta, A et al. "Phase Variation Analysis of *Coxiella burnetii* during Serial Passage in Cell Culture by Use of Monoclonal Antibodies"; Infection and Immunity (Aug. 2002), vol. 70, No. 8, pp. 4747-4749.
Palkovicova, K et al. "A monoclonal antibody specific for a unique biomarker, virenose, in a lipopolysaccharide of *Coxiella burnetii*"; Clinical Microbiology and Infection (Dec. 2009), vol. 15, Suppl: 2, pp. 183-184.
Flores-Ramirez, G et al. "In silico biosynthesis of virenose, a methylated deoxy-sugar unique to *Coxiella burnetii* lipopolysaccharide"; Proteome Science (2012), vol. 10:67, pp. 1-8.
Schramek, S et al. "3-C-Branched aldoses in lipopolysaccharide of phase I *Coxiella burnetii* and their role as immunodominant factors"; Eur. J. Biochem (1985), vol. 148: 455-461.

*Primary Examiner* — Padmavathi Baskar
(74) *Attorney, Agent, or Firm* — Knobbe, Martens, Olson & Bear, LLP (57) ABSTRACT

Vaccines and methods are for immunization against *Coxiella burnetii* infections and Q fever. The vaccine can be for protection against a *Coxiella burnetii* infection, or treating or preventing at least one symptom of Q fever. The vaccine includes a delipidated *C. burnetii* polysaccharide derived from a cell wall lipopolysaccharide of *C. burnetii*. The vaccine can also be a conjugate vaccine for protection against a *Coxiella burnetii* infection, or treating or preventing at least one symptom of Q fever. The conjugate vaccine includes a delipidated *C. burnetii* polysaccharide derived from a cell wall lipopolysaccharide of *C. burnetii* linked to an immunogenic carrier.

12 Claims, 6 Drawing Sheets

VACCINE

FIELD OF THE ART

The present disclosure relates generally to vaccines, and methods of use thereof, for immunization against *Coxiella burnetii* infections and Q fever. More particularly the disclosure relates to vaccines comprising a delipidated *C. burnetii* polysaccharide, optionally conjugated to an immunogenic carrier, typically a protein. The immunogenic carrier protein is covalently linked to the delipidated *C. burnetii* polysaccharide for the purpose of eliciting a T cell-dependent immune response to the polysaccharide.

BACKGROUND

Q fever is a systemic infection caused by the obligate intracellular bacterium *Coxiella burnetii*. Infection is common in animals, including livestock and various wild animals, although animals are typically asymptomatic. However *C. burnetii* is readily transmitted to humans through a number of routes, principally inhalation, Disease presentation in humans varies widely, and may include acute febrile illness most often with pneumonia, headaches, profuse sweating and muscle pain, chronic complicated Q fever with endocarditis or vascular infection, and post-Q fever fatigue. Given the variability in individual responses to *C. burnetii* infection, diagnosis can be difficult, and may be based on a combination of exposure history, clinical examination, serology and molecular analysis (e.g. PCR).

If diagnosed in the acute stage, the Q fever can be treated with a relatively short course of antibiotics, such as doxycycline, but chronic Q fever, associated with prolonged debility and fatigue, is significantly more difficult to treat and has a high mortality rate.

There is a clear need in the art for an effective vaccine to prevent the development of Q fever, in particular for use in the most at risk individuals and populations such as those with regular exposure to domestic animals, livestock and other farm animals or wild animals.

The only Q fever vaccine currently available is Q-VAX®. Despite its efficacy, Q-VAX® is associated with significant toxicity. It is a very difficult vaccine for medical professionals to use and requires the patient to be pre-tested for prior exposure to *C. burnetii* before it can be employed safely. Its use in an already sensitized person will lead to significant side effects. Q-VAX® is a formaldehyde inactivated whole bacterial cell vaccine prepared from the "Henzerling" strain of *C. burnetii* which was originally isolated from a patient in Italy during World War 2.

The toxicity of Q-VAX® and the extreme caution required in deciding whether a subject is suitable to receive the vaccine, make its use problematic. There is a need for the development of a safer, less toxic vaccine for Q fever.

SUMMARY OF THE DISCLOSURE

According to a first aspect of the present disclosure there is provided a vaccine for protection against a *Coxiella burnetii* infection, the vaccine comprising a delipidated *C. burnetii* polysaccharide derived from a cell wall lipopolysaccharide of *C. burnetii*.

Typically, the delipidated polysaccharide is the O-specific polysaccharide obtained by removal of the lipid A component of the phase 1 cell wall lipopolysaccharide. The delipidated polysaccharide may be derivatized.

In a particular embodiment, the delipidated polysaccharide is conjugated to an immunogenic carrier. Typically, the immunogenic carrier is a protein or polypeptide. In one exemplary embodiment the immunogenic carrier protein is a tetanus toxoid. The delipidated polysaccharide may be conjugated to the carrier using a crosslinking agent.

In a particular embodiment, the vaccine protects a subject against fever associated with *C. burnetii* infection.

According to a second aspect of the disclosure there is provided a vaccine for treating or preventing at least one symptom of Q fever, the vaccine comprising a delipidated *C. burnetii* polysaccharide derived from a cell wall lipopolysaccharide of *C. burnetii*.

In a particular embodiment, the at least one symptom is fever.

Typically, the delipidated polysaccharide is the O-specific polysaccharide obtained by removal of the lipid A component of the phase 1 cell wall lipopolysaccharide. The delipidated polysaccharide may be derivatized.

In a particular embodiment, the delipidated polysaccharide is conjugated to an immunogenic carrier. Typically, the immunogenic carrier is a protein or polypeptide. In one exemplary embodiment the immunogenic carrier protein is a tetanus toxoid. The delipidated polysaccharide may be conjugated to the carrier using a crosslinking agent.

According to a third aspect of the disclosure there is provided a conjugate vaccine for protection against a *Coxiella burnetii* infection, the vaccine comprising a delipidated *C. burnetii* polysaccharide derived from a cell wall lipopolysaccharide of *C. burnetii* linked to an immunogenic carrier.

The delipidated polysaccharide may be conjugated to the immunogenic carrier using a crosslinking agent. In an exemplary embodiment, the immunogenic carrier is a protein, such as a tetanus toxoid.

In a particular embodiment, the vaccine protects a subject against fever associated with *C. burnetii* infection.

According to a fourth aspect of the disclosure there is provided a conjugate vaccine for treating or preventing at least one symptom of Q fever, the vaccine comprising a delipidated *C. burnetii* polysaccharide derived from a cell wall lipopolysaccharide of *C. burnetii* linked to an immunogenic carrier.

In a particular embodiment, the at least one symptom is fever.

The delipidated polysaccharide may be conjugated to the immunogenic carrier using a crosslinking agent. In an exemplary embodiment, the immunogenic carrier is a protein, such as a tetanus toxoid.

According to a fifth aspect of the disclosure there is provided a method for preparing a non-toxic vaccine for protection against a *Coxiella burnetii* infection and/or for treating or preventing at least one symptom of Q fever, the method comprising linking a delipidated polysaccharide derived from a cell wall lipopolysaccharide of *C. burnetii* to an immunogenic carrier.

The delipidated polysaccharide may be conjugated to the immunogenic carrier using a crosslinking agent. In an exemplary embodiment, the immunogenic carrier is a protein, such as a tetanus toxoid.

In particular embodiments of the above aspects, the vaccine is not associated with adverse skin effects, such as induration or erythema, in a subject to which it is administered.

According to a sixth aspect of the disclosure there is provided a method for protecting a subject against a *Coxiella burnetii* infection, the method comprising administering to the subject an immunoprotective amount of a vaccine according to the first or second aspect.

According to a seventh aspect of the disclosure there is provided a method for treating or preventing at least one symptom of Q fever in a subject in need thereof, the method comprising administering to the subject an immunoprotective amount of a vaccine according to the first or second aspect.

Typically the subject is a human.

BRIEF DESCRIPTION OF THE DRAWINGS

Aspects and embodiments of the present disclosure are described herein, by way of non-limiting example only, with reference to the following drawings.

DETAILED DESCRIPTION

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

The articles "a" and "an" are used herein to refer to one or to more than one (i.e., to at least one) of the grammatical object of the article. By way of example, "an element" means one element or more than one element.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

In the context of the present specification, the terms "protein" and "polypeptide" may be used interchangeably herein.

As used herein the terms "treat" and "prevent", and the like, refer to any and all uses which remedy a condition or symptoms, prevent the establishment of a condition or disease, or otherwise prevent, hinder, retard, or reverse the progression of a condition or disease or one or more undesirable symptoms thereof in any way whatsoever. Thus the terms "treat" and "prevent" and the like are to be considered in their broadest context. For example, treatment does not necessarily imply that a subject is treated until total recovery. In conditions which display or a characterized by multiple symptoms, the treatment or prevention need not necessarily remedy, prevent, hinder, retard, or reverse all of said symptoms, but may prevent, hinder, retard, or reverse one or more of said symptoms. In the context of the present invention, symptoms that may be ameliorated, reversed, prevented, retarded or the linked include but are not limited to fever.

The term "subject" as used herein refers to a mammal, more particularly a human, who can benefit from a vaccine or method disclosed herein. The term "subject" as used herein also includes non-human primates, livestock animals (e.g. cattle, dairy cows, horses, sheep, pigs), laboratory test animals (e.g. mice, rabbits, rats, guinea pigs), companion animals (e.g. dogs, cats), wild animals and captive wild animals. A subject regardless of whether a human or non-human mammal may be referred to herein as an individual, subject, animal, patient, or recipient.

As used herein the term "immunoprotective" includes within its meaning a non-toxic but sufficient amount or dose of a composition or vaccine to elicit or induce a protective immune response in a subject. The exact amount or dose required will vary from subject to subject depending on factors such as the species being treated, the age and general condition of the subject, the particular vaccine being administered and the mode of administration and so forth. For any given case, an appropriate immunoprotective amount or dose may be determined by one of ordinary skill in the art using only routine experimentation.

*Coxiella burnetii* can exist in two molecular forms. Phase 1 is virulent and protective after infection, while phase 2 is avirulent and non-protective after infection. One difference between these two forms of the bacterium is in the length of the polysaccharide in the lipopolysaccharide (LPS) of the bacterial cell wall. In phase 1 the polysaccharide is long and contains unique monosaccharides (such as virenose), whereas in phase 2 it is short, lacks the unique monosaccharides and is made up of only "common" sugars. The phase 1 LPS is an important immunogenic molecule in *C. burnetii*.

The present invention is predicated on the inventors' surprising realisation that following removal of the lipid component from the cell wall LPS (delipidation), thereby eliminating the toxicity associated with the LPS, the delipidated polysaccharide can be used as the basis for a safe (non-toxic), efficacious vaccine against *C. burnetii* infection and Q fever, the immunogenicity of which can be enhanced by conjugation with a suitable carrier protein.

Accordingly, one aspect of the present disclosure provides a vaccine for protection against infection of *Coxiella burnetii*, the vaccine comprising a delipidated *C. burnetii* polysaccharide derived from a cell wall lipopolysaccharide of *C. burnetii*.

Also provided herein is a vaccine for treating or preventing at least one symptom of Q fever, the vaccine comprising a delipidated *C. burnetii* polysaccharide derived from a cell wall lipopolysaccharide of *C. burnetii*.

The term "vaccine" as used herein, is a broad term and is used in its ordinary sense, including, without limitation, delipidated *C. burnetii* polysaccharides or conjugates comprising delipidated *C. burnetii* polysaccharide linked to an immunogenic carrier, optionally formulated with adjuvants, diluents, excipients, carriers, and other pharmaceutically acceptable substances. The term "pharmaceutically acceptable" is used to refer to a non-toxic material that is compatible with a biological system such as a cell, cell culture, tissue, or organism.

In a particular embodiment the present disclosure provides vaccines in which the delipidated polysaccharide is the O-specific polysaccharide obtained by removal of the lipid A component of the phase 1 cell wall lipopolysaccharide.

*C. burnetii* cell wall lipopolysaccharides can be prepared according to standard techniques well known to those skilled in the art. Polysaccharides can be derived from naturally-occurring bacteria, genetically engineered bacteria, or can be produced synthetically. The polysaccharides are typically subjected to one or more processing steps prior to use, for example, purification, functionalization, depolymerization using mild acidic or oxidative conditions, deacetylation, and the like. Post processing steps can also be employed, if desired. Any suitable method known in the art for synthesizing, preparing, and/or purifying suitable polysaccharides and oligosaccharides can be employed.

As used herein, "delipidation" refers to the complete or substantial removal of lipids from a lipopolysaccharide to produce a delipidated polysaccharide. Where delipidation is substantial but not complete, the percentage of lipid component removed may be, for example, greater than 85%, 86%, 87%, 88%, 89%, 90%, 91%, 92%, 93%, 94%, 95%, 96%, 97%, 98% or 99%. In particular embodiments of the present disclosure, delipidation is such that the lipid A component of the phase 1 cell wall lipopolysaccharide of *C. burnetii* is removed.

Delipidation may be achieved by any suitable means. For example, the lipopolysaccharide may be treated with acetic acid or hydrazine, or any other agent or enzyme capable of removing ester-linked fatty acids from lipid A. A variety of suitable techniques are well known to those skilled in the art and are within the scope of the present disclosure.

In particular embodiments, in preparing a vaccine in accordance with the present disclosure the delipidated polysaccharide is covalently linked, or otherwise conjugated, to an immunogenic carrier molecule. Typically, the immunogenic carrier is a protein or polypeptide.

Any one of a variety of immunogenic carrier proteins may be employed. Suitable classes of proteins include pili, outer membrane proteins and excreted toxins of pathogenic bacteria; nontoxic or "toxoid" forms of such toxins, nontoxic proteins antigenically similar to bacterial toxins (i.e. cross-reacting materials or CRMs) and other proteins. Non-limiting examples of bacterial toxoids contemplated for use as immunogenic carrier proteins include tetanus toxin/toxoid, diphtheria toxin/toxoid, detoxified *P. aeruginosa* toxin A, cholera toxin/toxoid, pertussis toxin/toxoid and *Clostridium perfringens* exotoxins/toxoid. Other suitable bacterial proteins include, but are not limited to, pneumococcal surface protein A (PspA), pneumococcal adhesin protein (PsaA), and pneumococcal surface proteins BVH-3 and BVH-11. Suitable CRMs include $CRM_{197}$, antigenically equivalent to diphtheria toxin and CRM3201, a genetically manipulated variant of pertussis toxin. The use of immunogenic carrier proteins from non-mammalian sources including keyhole limpet hemocyanin, horseshoe crab hemocyanin and plant edestin is also contemplated, as is the use of viral proteins such as hepatitis B surface/core antigens; rotavirus VP7 protein and respiratory syncytial virus F and G proteins.

In an exemplary embodiment, the immunogenic carrier protein is tetanus toxoid.

Conjugation between the delipidated polysaccharide and the carrier can be achieved using a variety of reagents. The conjugation may be directly between the delipidated polysaccharide and the carrier protein, such as a direct covalent linkage by reductive amination. Alternatively, conjugation may be carried out using a cross-linking agent.

The cross-linking agent may be a bifunctional linker. In some instances, the presence of a spacer or linker may promote improved immunogenicity of the conjugate and more efficient coupling of the polysaccharide with the carrier. The length and flexibility of the linker can be adjusted as desired. Linkers also permit corresponding increases in translational and rotational characteristics of the antigens, increasing access of the binding sites to soluble antibodies. Suitable linkers which can be employed in accordance with the present disclosure include, but are not limited to, adipic acid dihydrazide (ADH), ε-aminohexanoic acid, diaminohexane, ε-amino-n-caproic acid, chiorohexanol dimethyl acetal, D-giucuronolactone and p-nitrophenyl amine. Coupling reagents include hydroxysuccinimides and carbodiimides. Many other linkers and coupling reagents known to those of ordinary skill in the art are also suitable for use in accordance with the present disclosure.

One exemplary method of conjugation comprises reacting the delipidated polysaccharide with adipic acid dihydrazide (ADH) to derivatize the polysaccharide, followed by reacting the carrier, such as tetanus toxoid, with 1-ethyl-3(3-dimethylaminopropy) carbodiimide (EDC) and adding to the derivatized delipidated polysaccharide. This method results in the formation of a covalently bonded aggregate of the delipidated polysaccharide-carrier conjugate.

The delipidated polysaccharide may undergo an activation step prior to being conjugated with the carrier. The term "activation" refers to a chemical treatment of the polysaccharide to provide chemical groups capable of reacting with the carrier (i.e. functionalizing the polysaccharide). One exemplary reagent for activation of the *C. burnetii* delipidated polysaccharide is 1-cyano-4-dimethylaminopyridinium tetrafluoroborate (CDAP). Those skilled in the art will appreciate that a variety of other known activation reagents and methodologies may be employed.

Also provide herein are methods for protecting subjects against *C. burnetii* infection and for treating or preventing at least one symptom of Q fever, comprising administering to the subjects a vaccine of the present disclosure.

Typically, the subject is a human. Of particular interest are those subjects most at risk of contracting a *C. burnetii* infection, such as those in regular or frequent contact with domestic animals, livestock (including abattoir workers), captive wild animals or other populations of wild animals.

The vaccine may be administered by any suitable route such as, for example, intramuscularly, subcutaneously, orally or intranasally. In particular embodiments, administration is intramuscular or subcutaneous. The immunoprotective amount of vaccine to be administered is typically determined on a case by case basis and may be determined by the skilled person without undue burden or the need for further invention. By way of example only, where the subject is a human, the immunoprotective amount may comprise between about 2 µg and about 200 µg, or between about 5 µg and about 50 µg, of a delipidated polysaccharide alone or a delipidated polysaccharide-carrier conjugate. For example, the immunoprotective amount may be about 2 µg, about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170 µg, about 180 µg, about 190 µg, or about 200 µg of a delipidated polysaccharide alone or a delipidated polysaccharide-carrier conjugate. Immunogenicity of the vaccine can be assessed and monitored by a range of techniques available to those skilled in the art, including the synthesis of antibodies in the subject subsequent to administration of the vaccine.

The immunoprotective amount of the vaccine may be administered in a single dose or in a series of doses. Where more than one dose is required, the doses may be administered days, weeks or months apart, such as for example, 4 weeks apart. Thus, the vaccines can be administered as a single dose or in a series including one or more boosters. In embodiments in which the vaccine comprises a delipidated polysaccharide-immunogenic carrier conjugate as described herein, typically only one or two doses of an immunoprotective amount of vaccine is required to achieve the desired protective or therapeutic effect.

The dosage of vaccine to be administered a subject and the regime of administration can be determined in accordance with standard techniques well known to those of ordinary skill in the pharmaceutical and veterinary arts, taking into consideration such factors as the intended use, particular antigen, the adjuvant (if present), the age, sex, weight, species, general condition, prior illness and/or treatments, and the route of administration. Preliminary doses can be determined according to animal tests, and the scaling of dosages for human administration is performed according to art-accepted practices such as standard dosing trials. The dosage depends on the specific activity of the conjugate and can be readily determined by routine experimentation.

Vaccine compositions of the present disclosure are typically sterile and may contain one or more pharmaceutically-acceptable carriers, such as one or more compatible solid or liquid fillers, diluents or encapsulating substances which are suitable for administration to a subject. Formulation of vaccines of the present disclosure into pharmaceutical compositions can be accomplished using methods known in the art. The vaccine compositions can also contain one or more adjuvants. Suitable adjuvants include, for example, aluminium adjuvants, such as aluminium hydroxide or aluminium phosphate, Freund's Adjuvant, BAY, DC-chol, pcpp, monophosphoryl lipid A, CpG, QS-21, cholera toxin and formyl methionyl peptide (see, e.g., Vaccine Design, the Subunit and Adjuvant Approach, 1995, M. F. Powell and M. J. Newman, eds., Plenum Press, N.Y.). A vaccine of the present disclosure may comprise one of more adjuvants. Exemplary adjuvants include aluminium compounds (alum), N-acetylmuramyl-L-alanyl-D-glutamine and other adjuvants known to those of ordinary skill in the art.

The vaccines may be in soluble or microparticular form or may be formulated, for example, in liposomes. Where the vaccine is to be administered parenterally, e.g. by intravenous, cutaneous, subcutaneous, or other injection, the vaccine is typically in the form of a pyrogen-free, parenterally acceptable aqueous or oily solution or suspension. The preparation of parenterally acceptable solutions with suitable pH, isotonicity, stability, and the like, is within the skill in the art. Suitable diluents include, for example, water, phosphate buffered saline (PBS) and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the preparation of injectable preparations.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the disclosure.

EXAMPLES

The following examples are illustrative of the disclosure and should not be construed as limiting in any way the general nature of the disclosure of the description throughout this specification.

Example 1

Cultivation and Purification of *Coxiella burnetii* Cells

*C. burnetii* strain Nine Mile, RSA 493, (Davis and Cox, Public Health Rep. 53:2259-2276, 1938) serologically in phase I (yolk sack passage 3 in our Laboratory) was propagated in six-seven-day-old embryonated hens' eggs. For inoculation, the stock suspension of *C. burnetii* infected yolk sacs (40%) in phosphate buffered saline (PBS) was used. The inoculum was from the Laboratory for Diagnosis and Prevention of Rickettsial and Chlamydial Infections, Institute of Virology, Slovak Academy of Sciences, Bratislava, Slovakia. The embryonated eggs were inoculated with a diluted infectious stock suspension (0.25 ml each) that resulted in the highest embryos' death 7-8 days post-inoculation. The inoculated eggs were incubated at 35.5° C. and relative humidity of 50-90%. From day 3, incubation was monitored twice daily with an ovoscope and evaluation of the yolk sacs by Gimenez-stained smears under a microscope. The yolk sacs with embryos that died within the first 72 hours were discarded. In the following days, the dead embryos were separated from the yolk sacs that were collected and stored at −20° C. On the day when 40-60% of remaining embryos were dead the cultivation was terminated. All yolk sacs infected with *C. burnetii* were deprived of embryos, collected and stored at −20° C.

After thawing, the *C. burnetii* infected yolk sacs were homogenized in a blender in an aqueous 1 M NaCl containing 0.2% phenol to 20% suspension that was allowed to stand at 5° C. for 3 days. The mixture was then centrifuged at 14,000×g, 20° C. for 40 minutes. The sediment was resuspended in aqueous 0.85% NaCl to 10% suspension and 2-3 volumes of ethyl ether were added. Partitioning between aqueous and organic phases was repeated several times until the aqueous layer containing *C. burnetii* cells became opalescent white and the Gimenez-stained smears revealed the pure *C. burnetii* cells only. The cells were centrifuged from aqueous phase at 10,000×g, 20° C. for 30 minutes, and stored at 5° C. as a 2 mg/ml suspension (adjusted photometrically at 420 nm) in PBS containing 0.1% phenol.

Example 2

Isolation and Detoxification of *C. burnetii* Lipopolysaccharide

*C. burnetii* cells (1.5 g) were suspended in 50 mM Tris-HCl buffer (150 ml, pH 7.5) and treated simultaneously with RNase (EC 3.1.27.5) and DNase (EC 3.1.27.1), both from bovine pancreas (Boehringer) at 37° C. for 16 hours. The cells were then treated with trypsin 1:250 (EC 232-650-8; Sigma) at 37° C. for 90 minutes followed by proteinase K from *Tritirachium album* (EC 3.4.21.14; Sigma) at 37° C. for 16 hours. After enzyme treatments, the cell suspension was centrifuged at 14,000×g, 10° C. for 50 minutes and the sediment was washed with acetone. Cells were extracted with chloroform-methanol (2:1, v/v) at 20° C. for 3 hours to remove phospholipids. The extraction was repeated with the fresh solvent mixture for 2 hours. The cell suspension was centrifuged at 3,000×g, 20° C. for 20 minutes and the sediment was suspended in preheated distilled water (150 ml, 68° C.) and extracted with an equal volume of aqueous 90% phenol as previously described (Westphal and Jann, 1965). A lipopolysaccharide (LPS) was obtained from the aqueous phase after extensive dialysis (molecular weight cut-off 3,500, Serva) and lyophilization. Yield of the crude LPS was 144 mg (9.6%) calculated on the weight of the original cells. LPS was further purified by treatments with RNase, DNase, and proteinase K (see above), dialyzed and lyophilized.

The protein and nucleic acid content of the purified LPS was less than 1%. Protein content was estimated colorimetrically according to the method of Hartree, 1972, and nucleic acids were determined spectrometrically. Phosphate, 3-deoxy-D-manno-oct-2-ulosonic acid (Kdo) and hexosamine contents of the LPS were 140.2, 98.6, and 288.5 nmol/mg, respectively. These were estimated colorimetrically according to the methods of Lowry et al., 1954 (phosphate), Brade et al., 1983 (Kdo), and Swann and Balazs, 1966 (hexosamine). Analysis of the constituent neutral sugars as the corresponding alditol acetates by gas chromatohraphy-mass spectrometry (GC-MS) revealed the presence of virenose (6-deoxy-3-C-methyl-D-gulopyranose), dihydrohydroxystreptose [3-C-(hydroxymethyl)-L-lyxofuranose] (Toman et al., 1998), D-mannose, D-glucose, and D-glycero-D-manno-heptose in 24.2, 14.5, 35.2, 1.5, and 24.6 (mole %), respectively.

LPS (120 mg) was hydrolyzed with aqueous 1% acetic acid (100 ml) at 100° C. for 90 minutes and the hydrolyzate was kept at −20° C. overnight. After melting, the precipitated lipid A was removed by low-speed centrifugation (9,300×g for 10 minutes). A solution of delipidated polysaccharide (delipidated O-specific polysaccharide or dOSP) was neutralized, extensively dialyzed (molecular weight cut-off 3,500, Serva) and lyophilized. Yield of dPS was 78.2 mg (65.2%). Phosphate, Kdo and hexosamine contents of the dOSP were 70.3, 45.2, and 312.6 nmol/mg, respectively. The protein and nucleic acid content of dOSP was less than 1%. Analysis of neutral sugars by GC-MS revealed virenose, dihydrohydroxystreptose, D-mannose, D-glucose, and D-glycero-D-manno-heptose in 21.1, 11.2, 37.3, 3.2, and 27.2 (mole %), respectively.

Example 3

Conjugation of Delipidated O-Specific Polysaccharide to a Carrier Protein

Detoxified (delipidated) Q Fever O-specific polysaccharide (dOSP), derived from its lipopolysaccharide (LPS) by removal of the toxic lipid A component, was conjugated to tetanus toxoid as a carrier protein. The primary purpose of the carrier protein is to improve the immunogenicity of the dOSP and to induce a T-cell dependent immune response when injected into animals.

Purified dOSP (Example 2) was activated with 1-cyano-4-dimethylaminopyridinium tetrafluoroborate (CDAP; Sigma) and derivatized with adipic acid dihydrazide (ADH; Sigma) using a modification of the method previously described (Konadu et al., 1996). Briefly the methodology was as follows dOSP was diluted to 5 mg/mL (2.0 mg/mL after addition of CDAP and ADH) in purified water and the pH adjusted to 5.1 to 5.5. CDAP (100 mg/ml in acetonitrile) was added to a final concentration of 2.0 mg/mL and held at room temperature (RT) for 2 minutes. The pH was then increased to around 8 by addition of 1.0 M sodium hydroxide (NaOH) (Sigma), ADH (90 mg/ml in 0.1 M NaHCO$_3$ (Sigma)) was then added to the reaction mixture to a final concentration of 9.0 mg/mL giving a ratio of dOSP:ADH of 1:4.5 (w/w). The reaction was allowed to proceed for 2 hours at RT, maintaining the pH between 8.0 and 8.5 during that time. The reaction mixture was then dialysed (MWCO 6-8 kD, Spectrum Laboratories) against 80 mM 2-(N-morpholino)ethanesulfonic acid (MES) (Sigma) pH 5.6 overnight at 4° C.

Tetanus toxoid (TT) was conjugated to the derivatised dOSP as follows. 1-ethyl-3-(3-dimethylaminopropyl)carbodiimide (EDC) (20 mg/ml in 80 mM 2-(N-morpholino)ethanesulfonic acid (MES) (Sigma) pH 5.6) was added to TT in 80 mM MES, the mixture was then added to derivatized dOSP so that the final concentrations of dOSP$_{AH}$:TT:EDC were 0.5:0.25:2.0 mg/ml respectively. The reaction was allowed to proceed for 3 hours at RT maintaining the pH between 5.5 and 5.8. At the end of the reaction the residual EDC was removed by dialysis (using a Sartorius-Stedim 300 kD Vivaspin) against 14 volume changes of phosphate buffered saline (PBS).

Example 4

Administration of *C. burnetii* Vaccines to Guinea Pigs

Guinea pigs were vaccinated with either a polysaccharide-carrier protein (dOSP-TT) conjugate vaccine or a polysaccharide (dOSP) only vaccine prior to infection with phase 1 *C. burnetii* Nine Mile strain. The guinea pig is the small laboratory animal of choice for Q fever studies because guinea pig infection with *C. burnetii* most closely follows acute human infection. Following infection the guinea pig develops fever for a few days and then recovers spontaneously, mirroring progression in most human infections. In contrast, most strains of laboratory mice do not show any symptoms of infection when infected with *C. burnetii*. In addition, some guinea pigs do not completely clear the infection, despite becoming asymptomatic, and can relapse with recrudescent infection at a later date if immunosuppressed. This is analogous to chronic Q fever in humans, where a person, after apparently recovering from acute Q fever, later relapses and develops chronic Q fever.

40 adult guinea pigs were divided into six experimental groups as follows:
Group 1—positive control; no vaccine; *C. burnetii* infection; n=8
Group 2—negative control; no vaccine; no infection; n=4
Group 3—vaccinated (single dose) with dOSP-TT conjugate vaccine prior to *C. burnetii* infection; n=8
Group 4—vaccinated (×2 doses) with dOSP-TT conjugate vaccine prior to *C. burnetii* infection; n=8
Group 5—vaccinated (single dose) with dOSP only vaccine prior to *C. burnetii* infection; n=6
Group 6—vaccinated (×2 doses) with dOSP only vaccine prior to *C. burnetii* infection; n=6

The first dose of vaccine (Groups 3, 4, 5 and 6) was administered on day 0 by intramuscular injection. The second dose in Groups 4 and 6 was administered on day 28 by intramuscular injection. Both doses comprised 30 μg vaccine. The challenge infection of *C. burnetii* (Groups 1 and 3-6) was administered on day 57 and consisted of $5 \times 10^5$ cells of viable, phase 1 *C. burnetii*, Nine Mile strain, grown in a mouse spleen, and inoculated intranasally as droplets while the guinea pig was anaesthetized.

Each guinea pig was examined daily from day −7 to day 0 (a week to allow the animals to acclimatize to their cages) and from day 0 to day 75. Each guinea pig temperature was taken daily by means of a subcutaneous temperature transponder. Guinea pig weight was measured twice weekly. General well-being was monitored continuously. The development of antibodies to *C. burnetii* and of local (skin) and systemic adverse events following injection of vaccine were also assessed.

The temperature changes of guinea pigs in each group over the course of the study are shown in FIGS. 1 to 6. The definition of "fever" was a temperature of 40° C. or higher. Fever after infection was detected only in Group 1 (positive control, no vaccine) and Group 5 (vaccinated ×1 with dOSP only vaccine). All other guinea pig groups were afebrile, including the negative control group 2. Numbers of febrile days in all groups are summarised in Table 1.

TABLE 1

Number of febrile days (T° ≥ 40° C.) in guinea pigs infected with $3.1 \times 10^6$ phase 1 *Coxiella burnetii*, intranasally, after vaccination

| | Number of febrile days in individual guinea pigs | | | | | | | Average (days) |
|---|---|---|---|---|---|---|---|---|
| Group 1 (n = 8) | 4 | 6 | 5 | 1 | 6 | 1 | 6 2 | 3.9 |
| Group 2 (n = 4) | 0 | 0 | 0 | 0 | | | | 0 |
| Group 3 (n = 8) | 0 | 3 | 2 | 0 | 0 | 2 | 0 | 1.0* (p = 0.005) |
| Group 4 (n = 8) | 0 | 0 | 0 | 0 | 8 | 3 | 1 | 1.7* (p = 0.031) |
| Group 5 (n = 6) | 3 | 3 | 2 | 2 | 3 | 4 | | 2.8 (p = 0.304) |
| Group 6 (n = 6) | 1 | 2 | 0 | 0 | 0 | 3 | | 1.0* (p = 0.007) |

*These vaccine groups had significantly reduced guinea pig febrile days compared to the unvaccinated positive control group.

In Group 1, where the guinea pigs were not vaccinated, but were infected, a guinea pig was febrile for 3.9 days, on average. Group 3 and Group 6 displayed a significantly reduced (p<0.007) number of febrile days. These results demonstrated that both the dOSP-TT conjugate vaccine and the dOSP only vaccine were effective in preventing fever in guinea pigs exposed to virulent *C. burnetii*, although only the dOSP-TT conjugate vaccine achieved this following a single dose of vaccine. In Group 5, where only 1 dose of dOSP only vaccine was administered, there was no protection from fever (p<0.3). This was expected in view of the known poor immunogenicity of polysaccharides.

Figure 1:
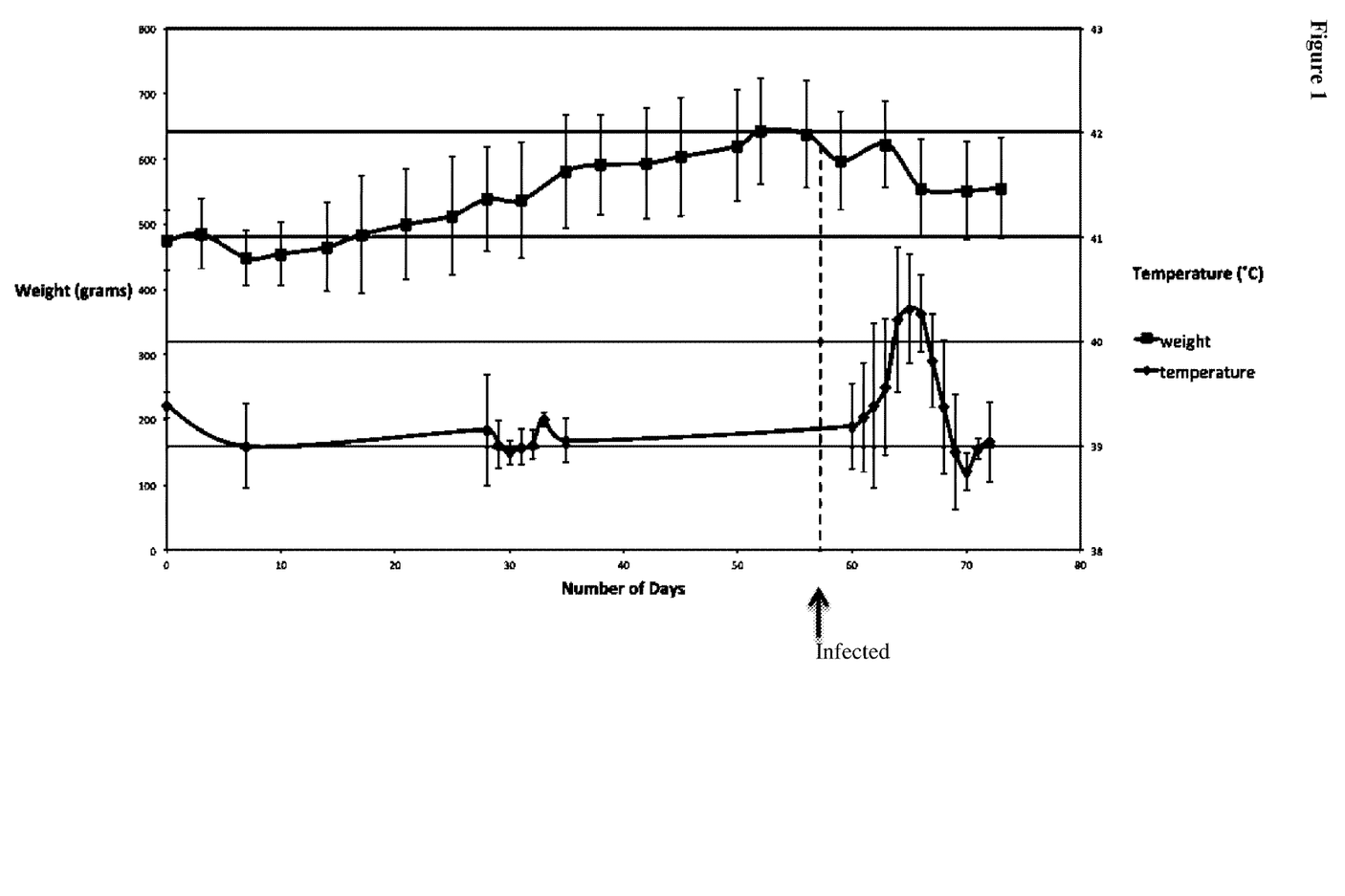
FIG. 1. Temperature and weight changes in guinea pigs (n=8) pre- and post-infection with phase 1 *C. burnetii* Nine Mile strain (Group 1 as described in Example 4). For temperature, each point on the graph represents the mean temperature +/−1 standard deviation on a particular day.
Figure 2:
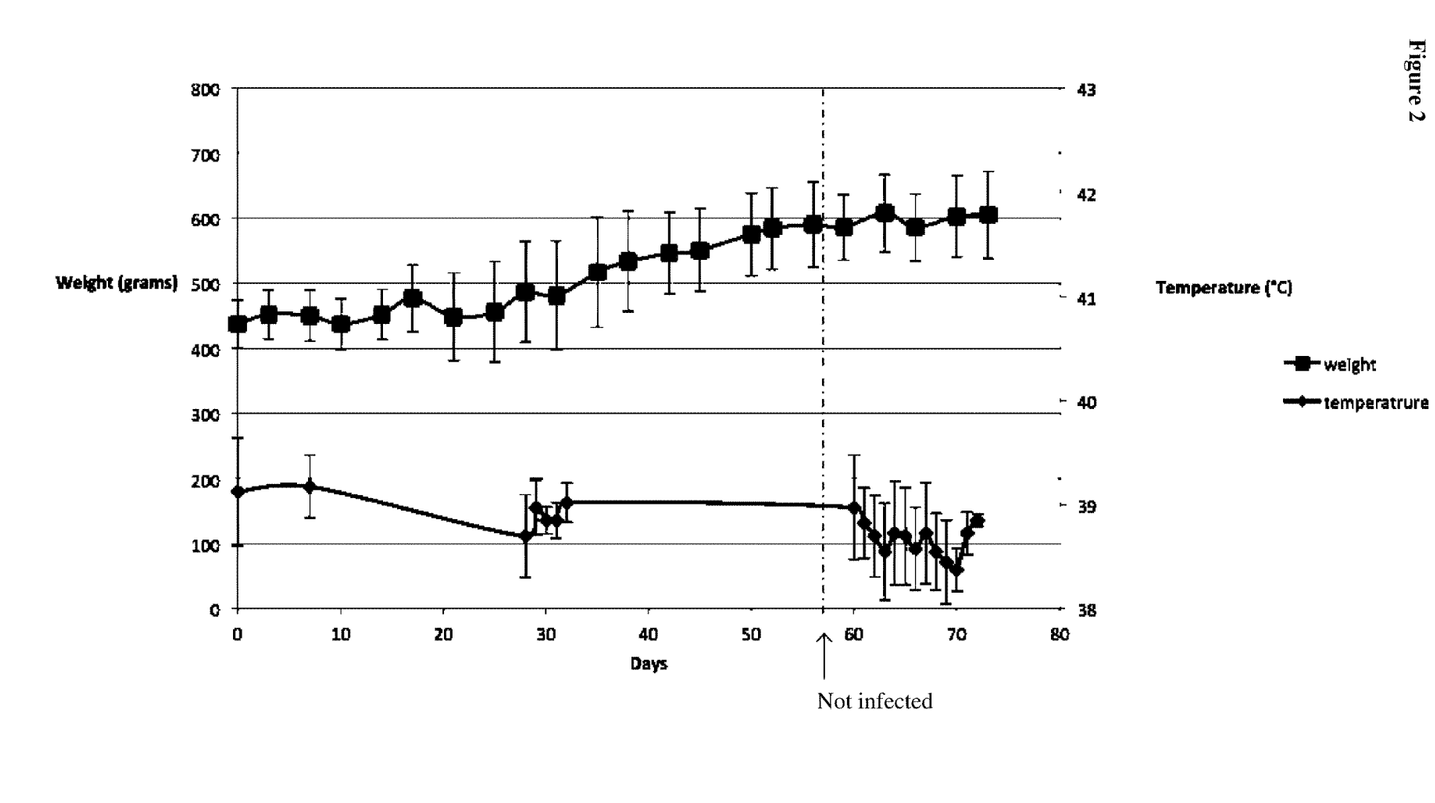
FIG. 2. Temperature and weight changes in guinea pigs (n=4) uninfected with *C. burnetii* (Group 2 as described in Example 4). For temperature, each point on the graph represents the mean temperature +/−1 standard deviation on a particular day.
Figure 3:
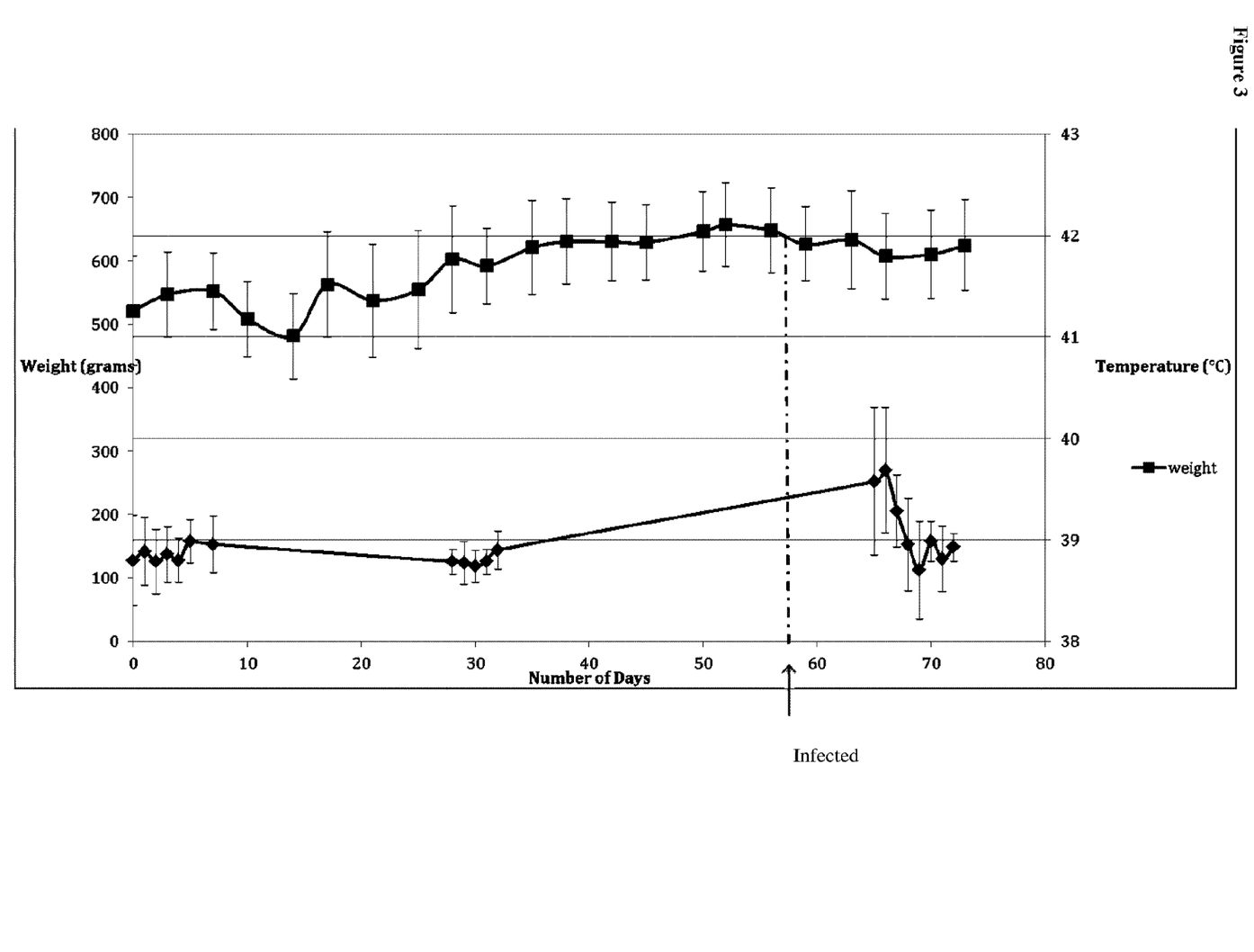
FIG. 3. Temperature and weight changes in guinea pigs (n=8) pre- and post-infection with phase 1 *C. burnetii* Nine Mile strain. The animals were vaccinated with a *C. burnetii* dOSP-TT conjugate vaccine on day 0 (Group 3 as described in Example 4). For temperature, each point on the graph represents the mean temperature +/−1 standard deviation on a particular day.
Figure 4:
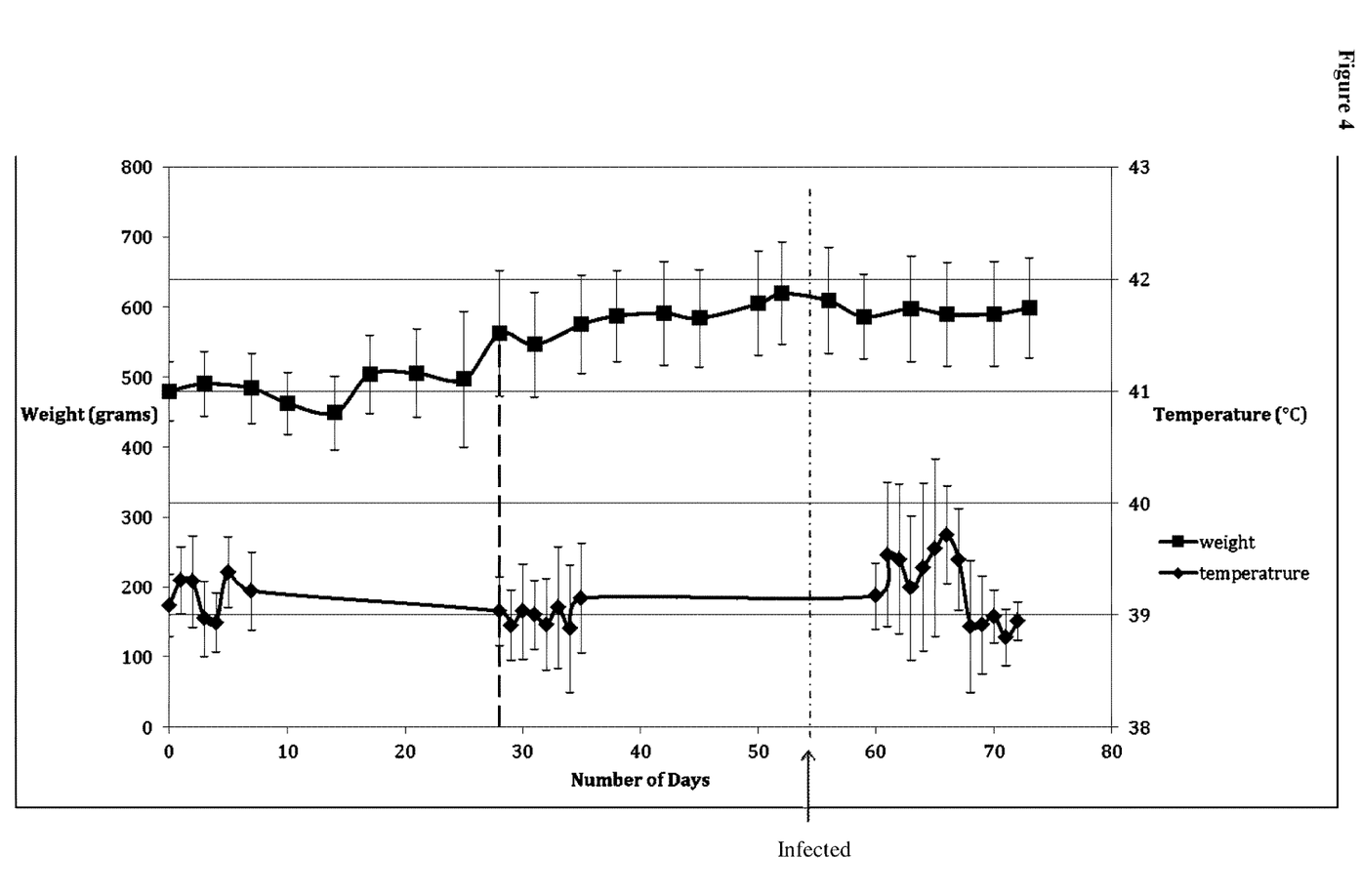
FIG. 4. Temperature and weight changes in guinea pigs (n=8) pre- and post-infection with phase 1 *C. burnetii* Nine Mile strain. The animals were vaccinated with a *C. burnetii* dOSP-TT conjugate vaccine on days 0 and 28 (Group 4 as described in Example 4). For temperature, each point on the graph represents the mean temperature +/−1 standard deviation on a particular day.
Figure 5:
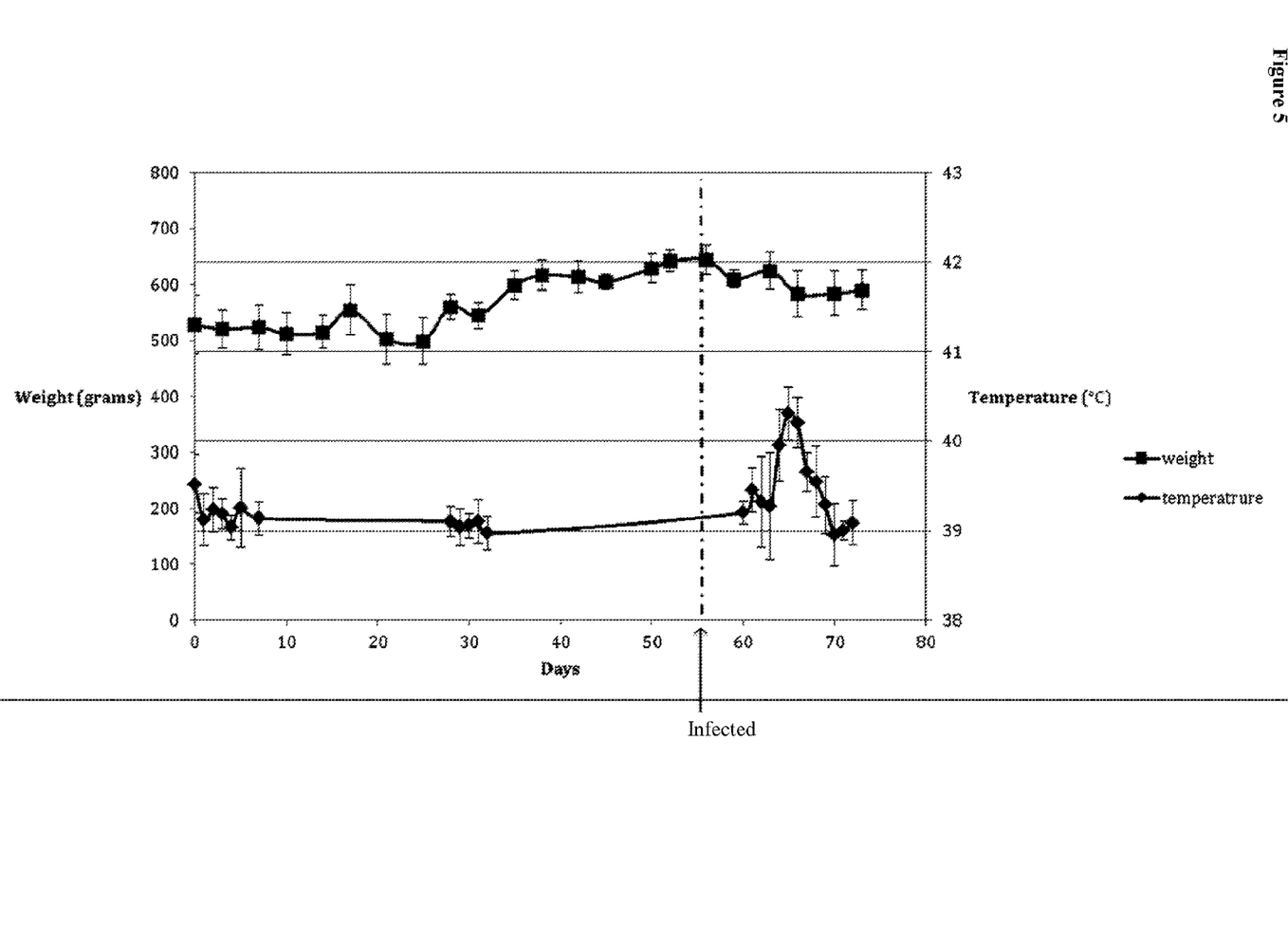
FIG. 5. Temperature and weight changes in guinea pigs (n=6) pre- and post-infection with phase 1 *C. burnetii* Nine Mile strain. The animals were vaccinated with a *C. burnetii* dOSP only vaccine on day 0 (Group 5 as described in Example 4). For temperature, each point on the graph represents the mean temperature +/−1 standard deviation on a particular day.
Figure 6:
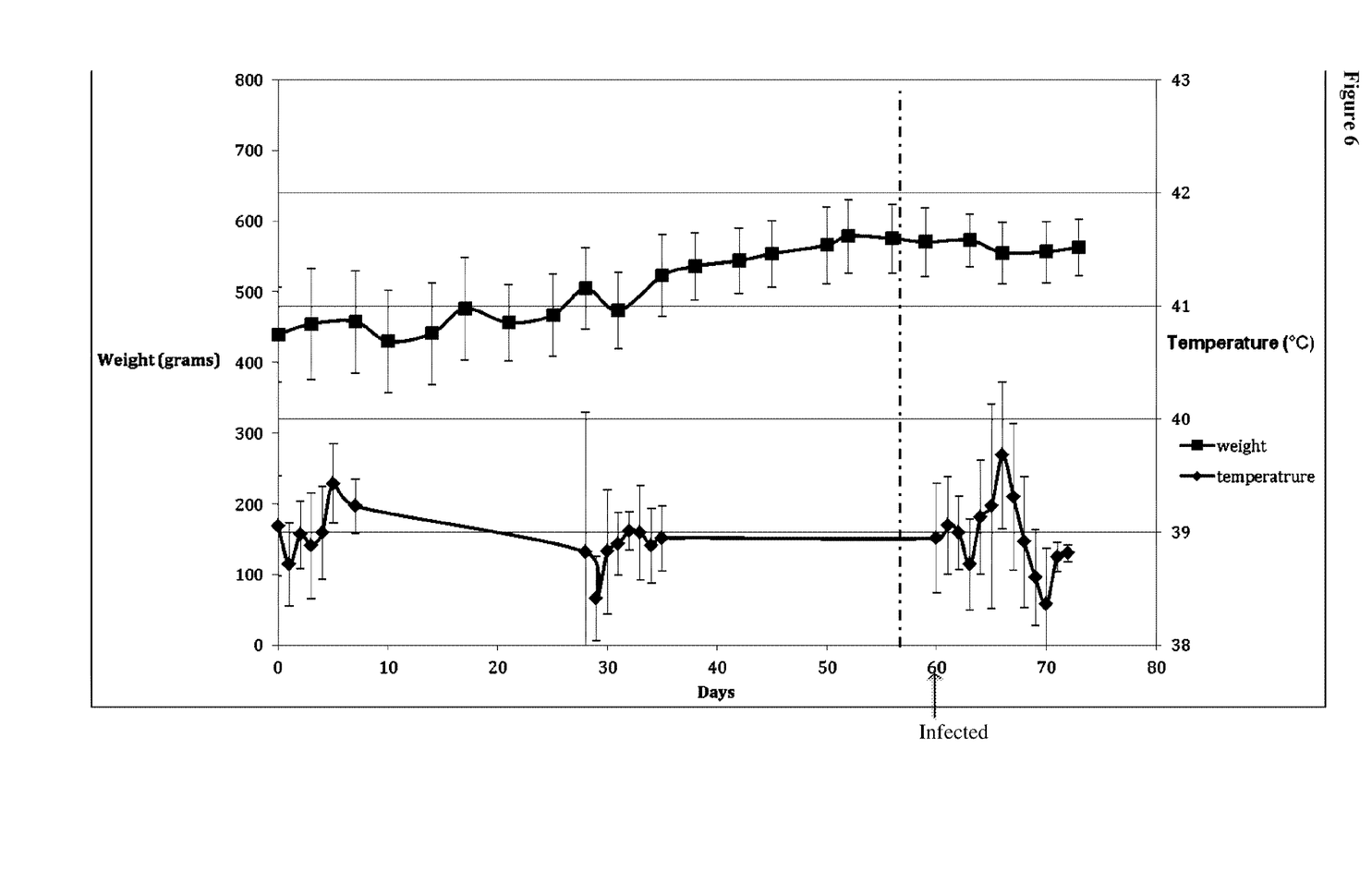
FIG. 6. Temperature and weight changes in guinea pigs (n=6) pre- and post-infection with phase 1 *C. burnetii* Nine Mile strain. The animals were vaccinated with a *C. burnetii* dOSP only vaccine on days 0 and 28 (Group 6 as described in Example 4). For temperature, each point on the graph represents the mean temperature +/−1 standard deviation on a particular day.

The weight changes of the guinea pigs in each group over the course of the study are shown in FIGS. 1 to 6. In the negative control group (Group 2), animals showed a steady weight gain until day 30, a rise in weight from days 30-55 and then had a steady weight until the end of the study (FIG. 2). In each of the vaccine groups (Groups 3 to 6) animals had similar weight curves, demonstrating that the vaccination and subsequent infection did not cause weight loss. However, in the positive control group (Group 1), there was a marked drop in weight from day 57, when animals were infected with *C. burnetii*. Thus, *C. burnetii* infection caused the guinea pigs to lose weight and condition, but not if they had been vaccinated beforehand. Clinical deterioration in infected guinea pigs was prevented by both the dOSP-TT conjugate vaccine and the dOSP only vaccine.

10 guinea pigs (selected from Groups 3 to 6) were examined for the development of phase 2 and phase 1 antibodies against *C. burnetii* by immunofluorescence, at a starting serum dilution of 1:25, 56 days after vaccination. *C. burnetii* cells, in both phase 1 and phase 2, were fixed onto wells on a glass slide. These cells were allowed to react with antibodies in the guinea pig sera. The starting dilution of the serum was 1:25 and higher dilutions (ie 1:50, 1:100, etc) were used until such reactivity was lost from the serum. The last positive dilution was referred to as the antibody titre for that guinea pig serum. A positive reaction was detected by fluorescence microscopy using fluorescein-labelled anti-guinea pig IgG serum, which reacted with the guinea pig antibodies attached to the *C. burnetii* cells. Results are shown in Table 2.

TABLE 2

Antibody response to *Coxiella burnetii* in guinea pigs after vaccination

| Vaccination group and guinea pig number | Antibody (IF) titre[1] | |
|---|---|---|
| | Phase 2 IgG | Phase 1 IgG |
| Group 3 | | |
| 1 | <25 | <25 |
| 2 | <25 | <25 |
| 3 | <25 | <25 |
| 4 | <25 | <25 |
| Group 4 | | |
| 11 | <25 | <25 |
| 12 | 400 | <25 |
| Group 5 | | |
| 24 | <25 | <25 |
| 25 | <25 | <25 |
| Group 6 | | |
| 30 | <25 | <25 |
| 31 | <25 | <25 |

[1]Antibody measured on day 56

Only one animal (#12 in Group 4) developed antibodies. Despite the absence of a humoral (antibody) immune response, the vaccinated guinea pigs were protected from infection with *C. burnetii*, pointing to the probable importance of cell-mediated immunity in this infection. This is consistent with the known intracellular location of the bacterium in the host animal and in humans. All guinea pigs were bled at the end of the study, just prior to being euthanised, and of 30 guinea pigs tested, only three had not produced antibodies, despite all having been infected with *C. burnetii* (Table 3).

TABLE 3

Antibody response to *Coxiella burnetii* in guinea pigs after vaccination and intranasal infection with *C. burnetii*

| Vaccination group and guinea pig number | Antibody titre[1] | |
|---|---|---|
| | Phase 2 IgG | Phase 1 IgG |
| Group 3 | | |
| 1 | ≥3200 | ≥3200 |
| 2 | 800 | 800 |
| 3 | <25 | <25 |
| 4 | ≥3200 | 800 |
| 5 | ≥3200 | 1600 |
| 6 | ≥3200 | 800 |
| 7 | ≥3200 | ≥3200 |
| Group 4 | | |
| 9 | 800 | 800 |
| 10 | ≥3200 | 400 |
| 11 | <25 | <25 |
| 12 | ≥3200 | 800 |
| 13 | ≥3200 | 1600 |
| 14 | ≥3200 | <25 |
| 15 | ≥3200 | 200 |
| Group 5 | | |
| 24 | 1600 | 200 |
| 25 | <25 | <25 |
| 26 | ≥3200 | 1600 |
| 27 | 100 | <25 |
| 28 | <25 | <25 |
| 29 | 200 | <25 |
| Group 6) | | |
| 30 | 1600 | 1600 |
| 31 | 1600 | 1600 |
| 32 | 1600 | <25 |
| 33 | 100 | <25 |
| 34 | 200 | <25 |
| Group 1 | | |
| 17 | ≥3200 | 400 |
| 18 | ≥3200 | 200 |
| 22 | ≥3200 | 200 |
| 23 | ≥3200 | ≥3200 |
| 27 | ≥3200 | 1600 |
| Group 2 | | |
| 36 | <25 | <25 |
| 38 | <25 | <25 |

[1]Serology using an indirect immunofluorescence assay on day 80

Eight guinea pigs which had been previously exposed to *C. burnetii* via vaccination and/or *C. burnetii* infection (2 animals from each of Groups 1, 3, 5 and 6) were subsequently injected subcutaneously with 0.1 ml of the dOSP-TT conjugate vaccine (15 ug). The study also included two non-immune guinea pigs that had never been exposed to *C. burnetii* (Group 2). Each animal was examined daily for 7 days after the injection of the vaccine for changes in behaviour and to assess if any induration or erythema developed in the skin. Results are shown in Table 4. No adverse reaction was seen in any animal, indicating that the dOSP-TT conjugate vaccine was not allergenic in the guinea pigs and it did not cause any adverse reaction in guinea pigs previously exposed to *C. burnetii*.

TABLE 4

Response of guinea pigs (Q fever vaccinated and infected with *Coxiella burnetii*), to subsequent intradermal injection[1] of conjugate vaccine

| Experimental vaccine group and guinea pig number | Local skin reaction[2] Days post intradermal injection | | | | | | |
|---|---|---|---|---|---|---|---|
| | 1 | 2 | 3 | 4 | 5 | 6 | 7 |
| Group 3 | | | | | | | |
| 4 | * | * | * | * | * | * | * |
| 6 | * | * | * | * | * | * | * |
| Group 5 | | | | | | | |
| 25 | * | * | * | * | * | * | * |
| 26 | * | * | * | * | * | * | * |
| Group 6 | | | | | | | |
| 35 | * | * | * | * | * | * | * |
| 36 | * | * | * | * | Died[3] | | |
| Group 1 | | | | | | | |
| 20 | * | * | * | * | * | * | * |
| 21 | * | * | * | Died[3] | | | |

TABLE 4-continued

Response of guinea pigs (Q fever vaccinated and infected with *Coxiella burnetii*), to subsequent intradermal injection[1] of conjugate vaccine

| Experimental vaccine group and guinea pig number | Local skin reaction [2] Days post intradermal injection | | | | | | |
|---|---|---|---|---|---|---|---|
| | 1 | 2 | 3 | 4 | 5 | 6 | 7 |
| Group 2 | | | | | | | |
| 36 | * | * | * | * | * | * | * |
| 39 | * | * | * | * | * | * | * |

[1] injection of conjugate vaccine (15 ug in 0.1 ml) on day 79
[2] erythema or induration
[3] guinea pig found dead in cage
* no erythema or induration

REFERENCES

Brade et al., *Eur J Biochem*, 131:195-200, 1983
Hartree, *Anal Biochem*, 48:422-427, 1972
Konadu et al., *Infect Immun*, 64:2709-2715, 1996
Lowry et al., *J Biol Chem*, 207:1-17, 1954
Swann and Balazs, *Biochim Biophys Acta*, 130:112-129, 1966
Toman et al., *Carbohyd Res*, 306:291-296, 1998
Westphal and Jann, *Meth Carbohydr Chem*, 5:83-91, 1965

The invention claimed is:

1. A vaccine for protection against a *Coxiella burnetii* infection, the vaccine comprising a delipidated *C. burnetii* polysaccharide derived from a cell wall lipopolysaccharide of *C. burnetii*, wherein the delipidated polysaccharide is the O-specific polysaccharide obtained by removal of the lipid A component of the phase 1 cell wall lipopolysaccharide and wherein the delipidated polysaccharide is conjugated to an immunogenic carrier.

2. The vaccine according to claim 1, wherein the vaccine protects a subject against fever associated with *C. burnetii* infection.

3. The vaccine according to claim 1, wherein the vaccine is for treating or preventing at least one symptom of Q fever.

4. The vaccine according to claim 1, wherein the carrier is a protein or polypeptide.

5. The vaccine according to claim 4, wherein the carrier is a tetanus toxoid.

6. The vaccine according to claim 1, wherein the delipidated polysaccharide is conjugated to the carrier using a crosslinking agent.

7. A conjugate vaccine for protection against a *Coxiella burnetii* infection, the vaccine comprising a delipidated *C. burnetii* polysaccharide derived from a cell wall lipopolysaccharide of *C. burnetii* linked to an immunogenic carrier, wherein the delipidated polysaccharide is the O-specific polysaccharide obtained by removal of the lipid A component of the phase 1 cell wall lipopolysaccharide.

8. The conjugate vaccine according to claim 7, wherein the vaccine protects a subject against fever associated with *C. burnetii* infection.

9. The conjugate vaccine according to claim 7, wherein the delipidated polysaccharide is conjugated to the carrier using a crosslinking agent.

10. The conjugate vaccine according to claim 7, wherein the carrier is a protein or polypeptide, optionally a tetanus toxoid.

11. A method for protecting a subject against a *Coxiella burnetii* infection or for treating or reducing at least one symptom of Q fever, the method comprising administering to the subject an immunoprotective amount of a vaccine comprising a delipidated *C. burnetii* polysaccharide derived from a cell wall lipopolysaccharide of *C. burnetii*, optionally linked to an immunogenic carrier, wherein the delipidated polysaccharide is the O-specific polysaccharide obtained by removal of the lipid A component of the phase 1 cell wall lipopolysaccharide.

12. A method for treating or reducing at least one symptom of Q fever in a subject in need thereof, the method comprising administering to the subject an immunoprotective amount of the conjugate vaccine according to claim 7.

* * * * *